US006184271B1

(12) United States Patent
Westland et al.

(10) Patent No.: US 6,184,271 B1
(45) Date of Patent: *Feb. 6, 2001

(54) ABSORBENT COMPOSITE CONTAINING POLYMALEIC ACID CROSSLINKED CELLULOSIC FIBERS

(75) Inventors: John A. Westland, Auburn; Richard A. Jewell, Bellevue; Amar N. Neogi, Seattle, all of WA (US)

(73) Assignee: Weyerhaeuser Company, Federal Way, WA (US)

( * ) Notice: Under 35 U.S.C. 154(b), the term of this patent shall be extended for 0 days.

This patent is subject to a terminal disclaimer.

(21) Appl. No.: 09/442,828

(22) Filed: Nov. 17, 1999

Related U.S. Application Data

(63) Continuation-in-part of application No. 08/989,697, filed on Dec. 12, 1997, now Pat. No. 5,998,511, which is a continuation of application No. 08/723,325, filed on Sep. 30, 1996, now Pat. No. 5,840,787, which is a continuation of application No. 08/218,106, filed on Mar. 25, 1994, now abandoned.

(51) Int. Cl.[7] .............................. C08L 1/02; A61F 13/15; A61F 13/20
(52) U.S. Cl. ..................... 524/13; 524/35; 525/54.21; 604/358; 604/365; 604/374; 604/904
(58) Field of Search ................... 524/13, 35; 525/54.21; 604/358, 365, 374, 904

(56) References Cited

U.S. PATENT DOCUMENTS

| | | | |
|---|---|---|---|
| 3,395,708 | 8/1968 | Hervey et al. | 128/284 |
| 3,440,135 | 4/1969 | Chung | 162/157 |
| 3,554,862 | 1/1971 | Hervey et al. | 162/158 |
| 3,658,613 | 4/1972 | Steiger | 156/153 |
| 3,677,886 | 7/1972 | Forsblad et al. | 162/172 |
| 3,731,411 | 5/1973 | Barber et al. | 38/144 |
| 3,819,470 | 6/1974 | Shaw et al. | 162/157 C |
| 3,854,866 | 12/1974 | Franklin et al. | 8/185 |
| 4,035,147 | 7/1977 | Sangenis et al. | 8/116.4 |
| 4,124,439 | 11/1978 | Dessauer | 162/146 |
| 4,144,122 | 3/1979 | Emanuelsson et al. | 162/158 |
| 4,303,471 | 12/1981 | Laursen | 162/158 |
| 4,351,699 | 9/1982 | Osborn, III | 162/112 |
| 4,431,481 | 2/1984 | Drach et al. | 162/157.6 |
| 4,476,323 | 10/1984 | Hellsten et al. | 564/284 |
| 4,822,453 | 4/1989 | Dean et al. | 162/187 |
| 4,853,086 | 8/1989 | Graef | 162/157.6 |
| 4,889,595 | 12/1989 | Herron et al. | 162/157.6 |
| 4,913,773 | 4/1990 | Knudsen et al. | 162/124 |
| 4,935,022 | 6/1990 | Lash et al. | 604/368 |
| 5,137,537 | 8/1992 | Herron et al. | 162/158.6 |
| 5,183,707 | 2/1993 | Herron et al. | 162/158 |
| 5,190,563 | 3/1993 | Herron et al. | 162/156.7 |
| 5,217,445 | 6/1993 | Young et al. | 609/381 |
| 5,225,047 | 7/1993 | Graef et al. | 162/9 |
| 5,256,746 | 10/1993 | Blankenship et al. | 526/223 |
| 5,308,896 | 5/1994 | Hansen et al. | 524/13 |
| 5,427,587 | 6/1995 | Arkens et al. | 81/16.1 |
| 5,447,977 | 9/1995 | Hansen et al. | 524/13 |
| 5,496,476 | 3/1996 | Tang et al. | 8/120 |
| 5,496,477 | 3/1996 | Tang et al. | 525/8.6 |
| 5,549,791 | 8/1996 | Herron et al. | 162/157.6 |
| 5,755,828 | 5/1998 | Westland | 8/185 |

FOREIGN PATENT DOCUMENTS

| | | |
|---|---|---|
| 0 252 649 A2 | 1/1988 | (EP) . |
| 0 440 472 | 1/1991 | (EP) . |
| 0 429 112 | 5/1991 | (EP) . |
| 2234422 | 6/1974 | (FR) . |
| WO 95/34710 | 12/1995 | (WO) . |
| WO 97/00354 | 1/1997 | (WO) . |
| WO 98/30387 | 7/1998 | (WO) . |

OTHER PUBLICATIONS

Blanchard, E.J., et al., "Dyeable Durable Press Cottons Finished with Citric Acid and Nitrogenous Additives," International Conference, American Association of Textile Chemists and Colorists, 1992.

Blanchard, E.J., et al., "Dyeable Cross-Linked Cellulose from Low Formaldehyde and Non-Formaldehyde Finishing Systems," *Industrial and Engineering Chemistry*, vol. 33, No. 4, pp. 1030–1034, 1994.

Carter, M.E., "Chemical Modification via Crosslinking Reactions," Essential Fiber Chemistry, Marcel Dekker, New York, 1991, pp. 8–18.

Carter, M.E., "Dyeing," Essential Fiber Chemistry, Marcel Dekker, New York, 1991, pp. 18–21.

"HBA—Weyerhaeuser Paper Company Introduces High Bulk Additive," brochure available from Weyerhaeuser Company, Tacoma, WA, 1990.

Carter, M.E., "Other Finished Treatments," Essential Fiber Chemistry, Marcel Dekker.

Neogi, A.N., et al., "Wet Strength Improvement via Fiber Surface Modification," *TAPPI*, vol. 63, No. 8, Aug. 1980, pp. 86–88.

Yang, Charles Q., "Infrared Spectroscopy Studies of the Cyclic Anhydride as the Intermediate for the Ester Crosslinking of Cotton Cellulose by Polycarboxylic Acids. I. Identification of the Cyclic Anhydride Intermediate," *Journal of Polymer Science: Part A: Polymer Chemistry*, vol. 31, 1993, pp. 1187–1193.

*Primary Examiner*—Peter A. Szekely
(74) *Attorney, Agent, or Firm*—Christensen O'Connor Johnson Kindness

(57) ABSTRACT

Cellulosic fibers intrafiber crosslinked with a polymeric polycarboxylic acid crosslinking agent are disclosed. In one embodiment, the polymeric polycarboxylic acid is polyacrylic acid and, in another embodiment, the polycarboxylic acid is polymaleic acid. Methods for forming cellulosic fibers having stable intrafiber crosslinks and for forming crosslinked cellulosic fibers having low knot level are also disclosed.

20 Claims, No Drawings

ABSORBENT COMPOSITE CONTAINING POLYMALEIC ACID CROSSLINKED CELLULOSIC FIBERS

CROSS-REFERENCE TO RELATED APPLICATIONS

This application is a continuation of U.S. patent application Ser. No. 08/989,697, filed Dec. 12, 1997, now U.S. Pat. No. 5,998,511, which is a continuation-in-part of U.S. patent application Ser. No. 08/723,325, filed Sep. 30, 1996, now U.S. Pat. No. 5,840,787, which is a continuation-in-part of Ser. No. 08/218,106, filed Mar. 25, 1994, now abandoned, the priority of the filing dates of which is hereby claimed under 35 U.S.C. §120. Each application is expressly incorporated herein by reference.

FIELD OF THE INVENTION

The present invention relates generally to crosslinked cellulosic fibers and more particularly, to cellulosic fibers crosslinked with polymeric polycarboxylic acid crosslinking agents, methods for producing such fibers, and absorbent structures containing polymeric polycarboxylic acid crosslinked fibers.

BACKGROUND OF THE INVENTION

Cellulose products such as absorbent sheets and other structures are composed of cellulose fibers which, in turn, are composed of individual cellulose chains. Commonly, cellulose fibers are crosslinked to impart advantageous properties such as increased absorbent capacity, bulk, and resilience to structures containing cellulose fibers. High-bulk fibers are generally highly crosslinked fibers characterized by high absorbent capacity and high resilience.

Crosslinked cellulose fibers and methods for their preparation are widely known. Tersoro and Willard, *Cellulose and Cellulose Derivatives,* Bikales and Segal, eds., Part V, Wiley-InterScience, New York, (1971), pp. 835–875. Most commonly, the term "crosslinked cellulose fiber" refers to a cellulose fiber having intrafiber crosslinks, i.e., crosslinks between individual cellulose chains within a single cellulose fiber. Generally, intrafiber crosslinks are formed by curing a crosslinking agent in the presence of the fibers. "Curing" refers to covalent bond formation (i.e., crosslink formation) between the crosslinking agent and the fiber. Crosslinking agents are generally bifunctional compounds, and in the context of cellulose crosslinking, these agents covalently couple a hydroxy group of one cellulose chain to another hydroxy group on a neighboring cellulose chain. Many crosslinking agents have been utilized in cellulose crosslinking achieving varying degrees of success.

Common cellulose crosslinking agents include aldehyde and urea-based formaldehyde addition products. See, for example, U.S. Pat. Nos. 3,224,926; 3,241,533; 3,932,209; 4,035,147; and 3,756,913. While these crosslinking agents have been widely used in some environments, their applicability to absorbent products that contact human skin (e.g., diapers) has been limited by safety concerns. These crosslinkers are known to cause irritation to human skin. Moreover, formaldehyde, which persists in formaldehyde-crosslinked products, is a known health hazard and has been listed as a carcinogen by the EPA. Accordingly, the disadvantages associated with formaldehyde and other formaldehyde-derived crosslinking agents has prompted the development of safer alternatives.

Other aldehyde crosslinking agents are also known. For example, dialdehyde crosslinking agents (i.e., $C_2$–$C_8$ dialdehydes and preferably glutaraldehyde) have also been utilized in the production of absorbent structures containing crosslinked cellulose fibers. See, for example, U.S. Pat. Nos. 4,689,118 and 4,822,453. While these dialdehyde crosslinkers appear to overcome the health risks associated with formaldehyde crosslinkers, these crosslinking agents suffer from commercial disadvantages related to the costs of producing dialdehyde crosslinked fibers.

Cellulose has also been crosslinked by carboxylic acid crosslinking agents. Certain polycarboxylic acids have been used to provide absorbent structures that have the polycarboxylic acid reacted with fibers in the form of intrafiber crosslink bonds. For example, U.S. Pat. Nos. 5,137,537, 5,183,707, and 5,190,563 describe the use of $C_2$–$C_9$ polycarboxylic acids crosslinking agents. These $C_2$–$C_9$ polycarboxylic acids are low molecular weight polycarboxylic acids that contain at least three carboxyl groups, and have from two to nine carbons in the chain or ring separating two of the carboxyl groups. Exemplary $C_2$–$C_9$ polycarboxylic acids include 1,2,3-tricarboxypropane, 1,2,3,4-tetracarboxybutane, and oxydisuccinic acid. A particularly preferred $C_2$–$C_9$ poly carboxylic acid is 2-hydroxy-1,2,3-tricarboxypropane, also known as citric acid. Unlike the aldehyde-based crosslinking agents noted above, these polycarboxylic acids are nontoxic and, for the preferred polycarboxylic acid citric acid, the crosslinking agent is commercially available at relatively low cost. Moreover, while the aldehyde-based crosslinking agents form relatively unstable acetal crosslinked bonds, $C_2$–$C_9$ polycarboxylic acid crosslinking agents provide relatively stable ester crosslinks.

While some of the disadvantages associated with the crosslinking agents noted above have been overcome by the development and utilization of new and improved crosslinking agents, crosslinking agents are generally characterized by their relatively narrow cure temperature range. The length of time at a particular cure temperature is also a factor in crosslinking fibers. The narrow cure temperature range of traditional crosslinking agents, such as those noted above, is due to their chemical reactivity. Most crosslinking agents have bifunctional reactivity and will undergo crosslinking at a temperature sufficient to cause the functional groups of the crosslinking agent (e.g., the aldehyde group of formaldehyde, or a carboxylic acid group of citric acid) to react with crosslink sites of the cellulose fiber (i.e., a hydroxy group). Generally, crosslinking occurs rapidly once a temperature sufficient to effect bond formation between the agent and fibers is reached.

Accordingly, there is a need in the art for a crosslinking agent that allows for greater flexibility in the production of crosslinked fibers having specific, desirable properties. More specifically, there exists a need for a safe and economical crosslinking agent curable over a wide temperature range to provide crosslinked fibers having a correspondingly wide range of crosslinking and associated advantageous absorbent properties.

Despite the advantages that polycarboxylic acid crosslinking agents provide, certain crosslinked cellulosic fibers, particularly cellulosic fibers crosslinked with low molecular weight polycarboxylic acids such as citric acid, tend to lose their crosslinks over time and revert to uncrosslinked fibers. For example, citric acid crosslinked fibers show a considerable loss of crosslinks on storage. Such a reversion of crosslinking generally defeats the purpose of fiber crosslinking, which is to increase the fiber's bulk and capacity. Thus, the useful shelf-life of fibers crosslinked with these polycarboxylic acids is relatively short and renders the fibers somewhat limited in their utility.

The loss of crosslinking results in a loss of the advantageous properties imparted to the fibers by crosslinking. Aged fibers, that is, fibers that have been subject to crosslinking reversion, can be characterized as having relatively lower bulk, diminished absorbent capacity, and lower liquid acquisition capability compared to the same fibers as originally formed.

Accordingly, there exists a need for stable intrafiber crosslinked cellulose fibers that offer the absorbent properties and advantages afforded by traditional crosslinked fibers and that also retain their intrafiber crosslinks over time and in storage to provide a crosslinked fiber having a substantial useful shelf-life. The present invention seeks to fulfill these needs and provides further related advantages.

SUMMARY OF THE INVENTION

In one aspect, the present invention provides individualized, chemically crosslinked cellulosic fibers comprising individualized cellulosic fibers intrafiber crosslinked with a polymeric polycarboxylic acid crosslinking agent. In one embodiment, the polymeric polycarboxylic acid crosslinking agent is an acrylic acid polymer and, in another embodiment, the polymeric polycarboxylic acid crosslinking agent is a maleic acid polymer. The polymeric polycarboxylic acid crosslinked fibers of the present invention are characterized as having high bulk, increased absorbent capacity, and enhanced liquid acquisition rates relative to noncrosslinked cellulosic fibers and fibers crosslinked with traditional crosslinking agents.

In another aspect of the present invention, a method for forming individualized, chemically intrafiber crosslinked cellulosic fibers is provided. In the method, a polymeric polycarboxylic acid crosslinking agent is applied to a mat of cellulosic fibers, the mat is then separated into unbroken individual fibers, and the individualized fibers are then dried and the crosslinking agent cured to form intrafiber crosslinks. Alternatively, in another embodiment, the fibers can be crosslinked (e.g., partially) in the mat prior to separation of the fibers and the formation of individual fibers.

Another aspect of the present invention provides a method for producing crosslinked fibers having absorbent properties that are dependent on the temperature at which the fibers are cured. In the method, the fibers are crosslinked with a polymeric polycarboxylic acid at a cure temperature between about 320° F. and about 380° F.

In yet another aspect, a method for forming crosslinked fibers having stable crosslinks is provided. In the method, cellulosic fibers are crosslinked with a polymeric polycarboxylic acid crosslinking agent.

In still another aspect, the present invention provides a method for forming crosslinked cellulosic fibers having a knot level significantly lower than other conventionally crosslinked fibers. In the method, cellulosic fibers are crosslinked with a polymaleic acid polymer crosslinking agent.

The present invention also provides absorbent structures that contain the individualized, polymeric polycarboxylic acid crosslinked fibers of this invention, and absorbent constructs incorporating such structures.

DETAILED DESCRIPTION OF THE PREFERRED EMBODIMENT

The present invention is directed to a polymeric polycarboxylic acid crosslinking agent for cellulose fibers, polymeric polycarboxylic acid crosslinked cellulose fibers, products containing these crosslinked fibers, and methods related to these fibers.

In one aspect, the present invention provides individualized, chemically crosslinked cellulosic fibers that have been intrafiber crosslinked with a polymeric polycarboxylic acid crosslinking agent. As used herein, the term "polymeric polycarboxylic acid" refers to a polymer having multiple carboxylic acid groups available for forming ester bonds with cellulose (i.e., crosslinks). Generally, the polymeric polycarboxylic acid crosslinking agents useful in the present invention are formed from monomers and/or comonomers that include carboxylic acid groups or functional groups that can be converted into carboxylic acid groups. Suitable crosslinking agents useful in forming the crosslinked fibers of the present invention include polyacrylic acid polymers, polymaleic acid polymers, copolymers of acrylic acid, copolymers of maleic acid, and mixtures thereof. Other suitable polymeric polycarboxylic acids include commercially available polycarboxylic acids such as polyaspartic, polyglutamic, poly(3-hydroxy)butyric acids, and polyitaconic acids. As used herein, the term "polyacrylic acid polymer" refers to polymerized acrylic acid (i.e., polyacrylic acid); "copolymer of acrylic acid" refers to a polymer formed from acrylic acid and a suitable comonomer, copolymers of acrylic acid and low molecular weight monoalkyl substituted phosphinates, phosphonates, and mixtures thereof; the term "polymaleic acid polymer" refers to polymerized maleic acid (i.e., polymaleic acid) or maleic anhydride; and "copolymer of maleic acid" refers to a polymer formed from maleic acid (or maleic anhydride) and a suitable comonomer, copolymers of maleic acid and low molecular weight monoalkyl substituted phosphinates, phosphonates, and mixtures thereof.

Polyacrylic acid polymers include polymers formed by polymerizing acrylic acid, acrylic acid esters, and mixtures thereof. Polymaleic acid polymers include polymers formed by polymerizing maleic acid, maleic acid esters, maleic anhydride, and mixtures thereof. Representative polyacrylic and polymaleic acid polymers are commercially available from, for example, the Rohm and Haas Company.

Examples of suitable polyacrylic acid copolymers include poly(acrylamide-co-acrylic acid), poly(acrylic acid-co-maleic acid), poly(ethylene-co-acrylic acid), and poly(1-vinylpyrrolidone-co-acrylic acid), as well as other polyacrylic acid derivatives such as poly(ethylene-co-methacrylic acid) and poly(methyl methacrylate-co-methacrylic acid). Suitable polymaleic acid copolymers include poly(methyl vinyl ether-co-maleic acid), poly(styrene-co-maleic acid), and poly(vinyl chloride-co-vinyl acetate-co-maleic acid). The representative polycarboxylic acid copolymers noted above are available in various molecular weights and ranges of molecular weights from commercial sources.

Generally, the polymeric polycarboxylic acids useful in the present invention include polymers having molecular weights in the range of from about 500 to about 40,000, and preferably from about 600 to about 10,000 grams/mole. Polyacrylic acid polymers preferably have molecular weights in the range of from about 1500 to about 15,000. Polymaleic acid polymers preferably have molecular weights in the range of from about 600 to about 1500. In contrast to the relatively high molecular weight polymaleic polycarboxylic acid crosslinking agents of the present invention, the $C_2$–$C_9$ polycarboxylic acids noted above have molecular weights no greater than about 350 g/mole.

As noted above, polycarboxylic acid copolymers are also useful for forming the crosslinked cellulose fibers of the present invention. Suitable polycarboxylic acid copolymers include copolymers of acrylic acid (i.e., acrylic acid copolymers) and copolymers of maleic acid (i.e., maleic acid copolymers) and have molecular weights ranging from about 500 to about 40,000, and more preferably from about 600 to about 2000 grams/mole. The weight ratio of acrylic or maleic acid to comonomer for these copolymers can range from about 10:1 to about 1:1, and more preferably from about 5:1 to about 2:1.

Suitable comonomers for forming polyacrylic and polymaleic acid copolymers include any comonomer that, when copolymerized with acrylic acid or maleic acid (or their esters), provides a polycarboxylic acid copolymer crosslinking agent that produces crosslinked cellulose fibers having the advantageous properties of bulk, absorbent capacity, liquid acquisition rate, and stable intrafiber crosslinks. Representative comonomers include, for example, ethyl acrylate, vinyl acetate, acrylamide, ethylene, vinyl pyrrolidone, methacrylic acid, methylylvinyl ether, styrene, vinyl chloride, itaconic acid, and tartrate monosuccinic acid. Preferred comonomers include vinyl acetate, methacrylic acid, methylvinyl ether, and itaconic acid. Polyacrylic and polymaleic acid copolymers prepared from representative comonomers noted above are available in various molecular weights and ranges of molecular weights from commercial sources. In a preferred embodiment, the polycarboxylic acid copolymer is a copolymer of acrylic and maleic acids.

The polycarboxylic acid polymers useful in forming the crosslinked fibers of the present invention include self-catalyzing polycarboxylic acid polymers. As used herein, the term "self-catalyzing polycarboxylic acid polymer" refers to a polycarboxylic acid polymer derivative that forms crosslinks with cellulose fibers at a practical rate at convenient cure temperatures without the aid of a crosslinking catalyst. Preferably, the self-catalyzing polycarboxylic acid crosslinking agent is a copolymer of either acrylic acid or maleic acid and low molecular weight monoalkyl substituted phosphinates and phosphonates. These copolymers can be prepared with hypophosphorous acid and its salts, for example, sodium hypophosphite, and/or phosphorus acids as chain transfer agents.

The polycarboxylic acid polymers and copolymers described above can be used alone, in combination, or in combination with other crosslinking agents known in the art.

Those knowledgeable in the area of polycarboxylic acid polymers will recognize that the polycarboxylic acid polymer crosslinking agents described above may be present in a variety of forms, such as the free acid form, and salts thereof Although the free acid form is preferred, it will be appreciated that all forms of the acid are included within the scope of the present invention. For embodiments of the invention that include a polymaleic acid polymer, a low pH polymaleic acid having a pH from about 2 to about 4 is preferred.

Cellulose fiber crosslinking with the polymeric polycarboxylic acid crosslinking agents described above can be accomplished at practical rates without a catalyst provided that the pH of the crosslinking reaction is maintained at acidic pH (i.e., pH ranges from about 1 to about 5). The effect of crosslinking solution pH on absorbent capacity of representative polymaleic acid crosslinked fibers formed in accordance with the present invention is described in Example 8. Preferably the pH of the crosslinking solution is maintained at a pH in the range of from about 2 to about 4.

Alternatively, the polymeric polycarboxylic acid crosslinking agents can be used with a crosslinking catalyst to accelerate the bonding reaction between the crosslinking agent and the cellulose fiber to provide the crosslinked cellulose fibers of this invention. Suitable crosslinking catalysts include any catalyst that increases the rate of ester bond formation between the polycarboxylic acid crosslinking agent and cellulose fibers. Preferred crosslinking catalysts include alkali metal salts of phosphorous containing acids such as alkali metal hypophosphites, alkali metal phosphites, alkali metal polyphosphonates, alkali metal phosphates, and alkali metal sulfonates. Particularly preferred catalysts include alkali metal polyphosphonates such as sodium hexametaphosphate and alkali metal hypophosphites such as sodium hypophosphite. The crosslinking catalyst is typically present in the crosslinking reaction in an amount in the range of from about 5 to about 20 weight percent of the crosslinking agent. Preferably, the catalyst is present in an amount of about 10 percent by weight of the crosslinking agent. A representative method for forming crosslinked cellulosic fibers with the aid of a catalyst is described in Example 2.

In such a method, the crosslinking catalyst is applied to the cellulose fibers in a manner analogous to application of the crosslinking agent to the fibers as described above. The crosslinking catalyst may be applied to the fibers prior to, after, or at the same time as the crosslinking agent is applied to the fibers. Accordingly, the present invention provides a method of producing crosslinked fibers that includes curing the crosslinking agent in the presence of a crosslinking catalyst.

Generally, the crosslinking catalyst promotes the formation of ester bonds between the polycarboxylic acid and the cellulose fiber. The catalyst is effective in increasing the degree of crosslinking (i.e., the number of ester bonds formed) at a given cure temperature. For example, as illustrated in Example 2, the level of crosslinking (as assessed by absorbent capacity) achieved at 360° F. without a catalyst is comparable to the crosslinking level achieved with a catalyst at 330° F. In other words, at a given cure temperature, the use of a crosslinking catalyst provides increased crosslinking. The preparation and properties of cellulose fibers crosslinked with a representative polycarboxylic acid crosslinking agent and crosslinking catalyst are described in Example 2.

The crosslinked cellulose fibers of the present invention have an effective amount of a polycarboxylic acid crosslinking agent reacted with the fibers to form intrafiber crosslinks. As used herein, "effective amount of a polycarboxylic acid polymer crosslinking agent" refers to an amount of crosslinking agent sufficient to provide an improvement in the absorbent properties (e.g., capacity, bulk, acquisition rate) or physical properties (e.g., stable intrafiber crosslink, low knot level) of the crosslinked fibers themselves, relative to conventional, uncrosslinked fibers, or fibers crosslinked with other crosslinking agents. Generally, the cellulose fibers are treated with a sufficient amount of a crosslinking agent such that an effective amount of crosslinking agent is reacted with the fibers.

The polymeric polycarboxylic acid crosslinking agent is preferably present on the fibers in an amount from about 1 to about 10% by weight of the total weight of the fibers. More preferably, the polymeric polycarboxylic acid is present in an amount from about 2 to about 8% by weight of the total fibers and, in a more preferred embodiment, from about 3 to about 6% by weight of the total fibers. The effect of amount of polymeric polycarboxylic acid on fiber bulk, capacity, and liquid acquisition rate is described in Examples 1, 5, and 6. Generally, increasing the amount of crosslinking agent on the fibers increases fiber bulk and capacity. Fibers crosslinked with 3–4% polymaleic acid generally have a liquid acquisition rate significantly greater than fibers similarly crosslinked with a representative urea-based crosslinking agent, DMDHEU.

As noted above, the present invention relates to cellulose fibers that are chemically intrafiber crosslinked with a polymeric polycarboxylic acid crosslinking agent. Although available from other sources, cellulosic fibers are derived primarily from wood pulp. Suitable wood pulp fibers for use with the invention can be obtained from well-known chemical processes such as the Kraft and sulfite processes, with or without subsequent bleaching. The pulp fibers may also be processed by thermomechanical, chemithermomechanical methods, or combinations thereof. The preferred pulp fiber is produced by chemical methods. Ground wood fibers, recycled or secondary wood pulp fibers, and bleached and unbleached wood pulp fibers can be used. The preferred starting material is prepared from long fiber coniferous wood species, such as southern pine, Douglas fir, spruce, and hemlock. Details of the production of wood pulp fibers are well-known to those skilled in the art. These fibers are commercially available from a number of companies, including Weyerhaeuser Company, the assignee of the present invention. For example, suitable cellulose fibers produced from southern pine that are usable with the present invention are available from Weyerhaeuser Company under the designations CF416, NF405, PL416, FR516, and NB416.

The wood pulp fibers useful in the present invention can also be pretreated prior to use with the present invention. This pretreatment may include physical treatment, such as subjecting the fibers to steam, or chemical treatment.

Although not to be construed as a limitation, examples of pretreating fibers include the application of fire retardants to the fibers, and surfactants or other liquids, such as water or solvents, which modify the surface chemistry of the fibers. Other pretreatments include incorporation of antimicrobials, pigments, and densification or softening agents. Fibers pretreated with other chemicals, such as thermoplastic and thermosetting resins also may be used. Combinations of pretreatments also may be employed.

Cellulosic fibers treated with particle binders and/or densification/softness aids known in the art can also be employed in accordance with the present invention. The particle binders serve to attach other materials, such as superabsorbent polymers, as well as others, to the cellulosic fibers. Cellulosic fibers treated with suitable particle binders and/or densification/softness aids and the process for combining them with cellulose fibers are disclosed in the following U.S. patents and patent applications: (1) U.S. Pat. No. 5,543,215, entitled "Polymeric Binders for Binding Particles to Fibers"; (2) U.S. Pat. No. 5,538,783, entitled "Non-Polymeric Organic Binders for Binding Particles to Fibers"; (3) U.S. Pat. No. 5,300,192, entitled "Wet Laid Fiber Sheet Manufacturing With Reactivatable Binders for Binding Particles to Binders;" (4) U.S. Pat. No. 5,352,480, entitled "Method for Binding Particle to Fibers Using Reactivatable Binders"; (5) U.S. Pat. No. 5,308,896, entitled "Particle Binders for High-Bulk Fibers"; (6) Ser. No. 07/931,279, filed Aug. 17, 1992, entitled "Particle Binders that Enhance Fiber Densification"; (7) Ser. No. 08/107,469, filed Aug. 17, 1993, entitled "Particle Binders"; (8) Ser. No. 08/108,219, filed Aug. 17, 1993, entitled "Particle Binding to Fibers"; (9) Ser. No. 08/107,467, filed Aug. 17, 1993, entitled "Binders for Binding Water Soluble Particles to Fibers"; (10) U.S. Pat. No. 5,547,745, entitled "Particle Binders"; (11) Ser. No. 08/108,218, filed Aug. 17, 1993, entitled "Particle Binding to Fibers"; and (12) U.S. Pat. No. 5,308,896, entitled "Particle Binders for High-Bulk Fibers," all expressly incorporated herein by reference.

The polymeric polycarboxylic acid crosslinking agent may be applied to the cellulose fibers by any one of a number of methods known in the production of treated fibers. For example, the polymeric polycarboxylic acid can be contacted with the fibers as a fiber sheet is passed through a bath containing the polycarboxylic acid. Alternatively, other methods of applying the polycarboxylic acid, including fiber spray, or spray and pressing, or dipping and pressing with a polycarboxylic acid solution, are also within the scope of the present invention.

Generally, the intrafiber crosslinking cellulose fibers of the present invention can be formed by applying the polymeric polycarboxylic acid crosslinking agent to the cellulose fibers, separating the treated mat into individual fibers, and then curing the crosslinking agent at a temperature sufficient to effect crosslink formation between the polymeric polycarboxylic acid and the cellulose fiber. The polymeric polycarboxylic acid crosslinking agent may be cured by heating the crosslinking agent-treated fiber at a temperature and for a time sufficient to cause crosslinking to occur. The rate and degree of crosslinking depend upon a number of factors including the moisture content of the fibers, temperature, and pH, as well as the amount and type of catalyst. Those skilled in the art will appreciate that time-temperature relationships exist for the curing of the crosslinking agent. Generally, the extent of curing, and consequently the degree of crosslinking, are a function of the cure temperature. The polymeric polycarboxylic acid crosslinking agents of the present invention are preferably cured at temperatures ranging from about 320° F. to about 380° F. The effect of cure temperature on the bulk and absorbent capacity of representative polymeric polycarboxylic acid crosslinked fibers is described in Examples 1, 2, 3, 5, and 8. Generally, crosslinked fiber bulk and absorbent capacity increase with increasing cure temperature.

In general, the cellulose fibers of the present invention may be prepared by a system and apparatus as described in U.S. Pat. No. 5,447,977 to Young, Sr. et al., which is incorporated herein by reference in its entirety. Briefly, the fibers are prepared by a system and apparatus comprising a conveying device for transporting a mat of cellulose fibers through a fiber treatment zone; an applicator for applying a treatment substance such as a polymeric polycarboxylic acid crosslinking agent from a source to the fibers at the fiber treatment zone; a fiberizer for completely separating the individual cellulose fibers comprising the mat to form a fiber output comprised of substantially unbroken cellulose fibers; and a dryer coupled to the fiberizer for flash evaporating residual moisture and for curing the crosslinking agent(s), to form dried and cured crosslinked fibers.

As used herein, the term "mat" refers to any nonwoven sheet structure comprising cellulose fibers or other fibers that are not covalently bound together. The fibers include fibers obtained from wood pulp or other sources including cotton rag, hemp, grasses, cane, husks, cornstalks, or other suitable sources of cellulose fibers that may be laid into a sheet. The mat of cellulose fibers is preferably in an extended sheet form, and may be one of a number of baled sheets of discrete size or may be a continuous roll.

Each mat of cellulose fibers is transported by a conveying device, for example, a conveyor belt or a series of driven rollers. The conveying device carries the mats through the fiber treatment zone.

At the fiber treatment zone the polymeric polycarboxylic acid crosslinking agent is applied to the cellulose fibers. The polymeric polycarboxylic acid is preferably applied to one or both surfaces of the mat using any one of a variety of methods known in the art including spraying, rolling, or dipping. Once the crosslinking agent has been applied to the mat, the crosslinking agent may be uniformly distributed through the mat, for example, by passing the mat through a pair of rollers.

After the fibers have been treated with the crosslinking agent, the impregnated mat is fiberized by feeding the mat through a hammermill. The hammermill serves to separate the mat into its component individual cellulose fibers, which are then blown into a dryer.

The dryer performs two sequential functions; first removing residual moisture from the fibers, and second curing the polymeric polycarboxylic acid crosslinking agent. In one embodiment the dryer comprises a first drying zone for receiving the fibers and for removing residual moisture from the fibers via a flash-drying method, and a second drying zone for curing the crosslinking agent. Alternatively, in another embodiment, the treated fibers are blown through a flash-dryer to remove residual moisture, and then transferred to an oven where the treated fibers are subsequently cured.

The crosslinked cellulose fibers of this invention exhibit advantageous absorbent characteristics including increased absorbent capacity, rate of absorption, bulk, and resilience (springback) relative to noncrosslinked fibers. Generally, the absorbent capacity of fibers (reported in units of grams water/gram fiber), the rate of absorption of water (mL/sec), bulk (cc/g), and resilience (i.e., the extent to which the crosslinked fibers spring back) increase with increasing crosslinking. For the crosslinked fibers of this invention, increased crosslinking may be achieved either by contacting the fiber to be crosslinked with increasing amounts and/or concentrations of crosslinking agent or, alternatively, by increasing the temperature at which the polymaleic acid treated fibers are cured. The preparation and some properties of some representative polymeric polycarboxylic acid crosslinked cellulose fibers of the invention are described in Example 1 (polyacrylic acid crosslinked fibers) and Examples 4–5 (polymaleic acid crosslinked fibers).

As noted above, the absorbent characteristics of crosslinked cellulose fibers formed in accordance with this invention are generally affected by the extent of crosslinking by the polymeric polycarboxylic acid crosslinking agent. Furthermore, it has been discovered that the extent of crosslinking by the polymeric polycarboxylic acid, and consequently the fibers' resulting absorbent properties can be controlled by the temperature used to cure the treated fibers (i.e., to cause ester bond formation). At higher cure temperature, more ester bonds are formed between the polymeric polycarboxylic acid and the fiber, and greater crosslinking results.

Thus, in another aspect, the present invention provides a method for forming crosslinked cellulosic fibers having absorbent properties that are dependent upon cure temperature. In the method, the crosslinked fibers are generally prepared as described above using a polymeric polycarboxylic acid crosslinking agent and then cured at a cure temperature in the range of from about 320° F. to about 380° F., the particular cure temperature selected to achieve the desired absorbent capacity, bulk, springback, and liquid acquisition rate characteristics. The effect of cure temperature variation on the properties of polyacrylic acid crosslinked fibers is described in Examples 1 and 2, and the effect of cure temperature of polymaleic acid crosslinked fibers is described in Example 5. As noted above, increasing cure temperature generally results in crosslinked fibers having increased bulk and absorbent capacity.

The polymeric polycarboxylic acid crosslinked fibers of the invention may be formed into sheets or mats having high absorbent capacity, bulk, and resilience. For example, these crosslinked fibers may be combined with other fibers including other crosslinked and noncrosslinked fibers. The sheets and mats comprised of polycarboxylic acid crosslinked fibers may be incorporated into a variety of absorbent products including, for example, tissue sheets, disposable diapers, sanitary napkins, tampons, and bandages.

The polymeric polycarboxylic acid crosslinked fibers formed in accordance with the present invention exhibit a density that remains substantially unchanged over the lifetime of fibrous webs prepared from these fibers. This resistance to aging or reversion of density relates to the stability of intrafiber crosslinks formed using polymeric polycarboxylic acid crosslinking agents. In contrast, cellulose fibers crosslinked with citric acid show a considerable increase in density, accompanied by a loss of bulk and absorbent capacity over time. Generally, the increase in density indicates a decrease in the level of crosslinking (i.e., reversion) in the fibers. In addition to density increase, the loss of crosslinking in the fibrous web results in a less bulky web and, consequently, diminished absorbent capacity and liquid acquisition capability. Accordingly, the present invention provides a method for forming cellulose fibers having stable intrafiber crosslinks that includes crosslinking cellulosic fibers with a polymeric polycarboxylic acid crosslinking agent as described above. Typically, the polymeric polycarboxylic acid crosslinked fibers have a reverted density increase of less than about 20% and, more preferably, less than about 10%. In contrast, citric acid crosslinked fibers have a reverted density increase of about 50%, which is significantly greater than the reverted density value of the fibers formed in accordance with the present invention. The effect of aging (i.e., reversion of crosslinking) on the density of fibrous webs composed of polyacrylic acid crosslinked fibers and fibrous webs composed of citric acid crosslinked fibers is described in Example 11. In addition, the wet bulk and absorbent capacity of polymaleic acid crosslinked fibers remain substantially unchanged in accelerated aging processes, indicating that fibers crosslinked with polymaleic acid also retain their crosslinks.

In another aspect of the present invention, a method for forming crosslinked fibers having a low knot level is provided. In the method, cellulosic fibers are crosslinked with a polymaleic acid polymer as generally described above. The resulting polymaleic acid crosslinked fibers typically have a knot level of less than about 10%, preferably less than about 5%. Fibers crosslinked with a representative urea-based crosslinking agent, DMDHEU, have a knot level of about 20%, which is significantly greater than the knot level of fibers formed in accordance with this invention. A comparison of knot level for polymaleic acid and DMDHEU crosslinked fibers is described in Example 7.

In another embodiment, the present invention provides cellulose fibers that are crosslinked with a blend of crosslinking agents that include the polymeric polycarboxylic acid described above and a second crosslinking agent. Preferably, the fibers are crosslinked with a second crosslinking agent having a cure temperature below that of the polymeric polycarboxylic acid. For this embodiment, suitable second crosslinking agents have a cure temperature below the cure temperature of the polymeric polycarboxylic acid crosslinking agents, i.e., below about 320° F. Preferred second crosslinking agents include urea-based derivatives such as, for example, methylolated urea, methylolated cyclic ureas, methylolated lower alkyl substituted cyclic ureas, dihydroxy cyclic ureas, lower alkyl substituted dihydroxy cyclic ureas, methylolated dihydroxy cyclic ureas. Other suitable urea derivatives include dimethyldihydroxy urea (DMDHU, 1,3-dimethyl-4,5-dihydroxy-2-imidazolidinone), dimethyloldihydroxyethylene urea (DMDHEU, 1,3-dihydroxymethyl-4,5-dihydroxy-2-imidazolidinone), dimethylol urea (DMU, bis[N-hydroxymethyl]urea), dihydroxyethylene urea (DHEU, 4,5-dihydroxy-2-imidazolidinone), dimethylolethylene urea (DMEU, 1,3-dihydroxymethyl-2-imidazolidinone), and dimethyldihydroxyethylene urea (DDI, 4,5-dihydroxy-1,3-dimethyl-2-imidazolidinone).

Other preferred second crosslinking agents include polycarboxylic acids including, for example, citric acid, tartaric acid, maleic acid, succinic acid, glutaric acid, citraconic acid, maleic acid (and maleic anhydride), itaconic acid, and tartrate monosuccinic acid. In more preferred embodiments, the second crosslinking agent is citric acid or maleic acid (or maleic anhydride). Other preferred second crosslinking agents include glyoxal and glyoxylic acid.

While the composition of the crosslinking blend can be varied to form crosslinked cellulosic fibers having desired properties, the polymeric polycarboxylic acid is the predominant crosslinking agent in the blend. The second crosslinking agent is generally present in the blend in the amount of from about 5 to about 50 percent by weight of the total crosslinking blend.

The characteristics of representative crosslinked cellulose fibers prepared from blends of polyacrylic acid and maleic acid and polyacrylic acid and citric acid are described in Examples 3 and 10, respectively. Generally, the bulk and absorbent capacity of cellulose fibers crosslinked with polymeric polycarboxylic acid blends is greater than fibers crosslinked with either the polycarboxylic acid or the second crosslinking agent alone. Furthermore, the problem associated with discoloration to crosslinked fibers crosslinked with citric acid alone is improved by using a polymeric polycarboxylic acid blend without sacrificing the beneficial aspects of the fibers' absorbent capacity. Cellulosic fibers crosslinked with a blend of a polymeric polycarboxylic acid and citric acid have been found to have improved brightness relative to fibers crosslinked with citric acid alone. In addition, the resistance of polymeric polycarboxylic acid crosslinked fibers to reversion, i.e., the loss of crosslinks, imparts stability to fibers crosslinked with polymeric polycarboxylic acid blends. For example, while cellulose fibers crosslinked with citric acid alone are highly susceptible to crosslink reversion, fibers crosslinked with blends of citric acid and a polymeric polycarboxylic acid exhibit advantageous absorbent properties and stable crosslinks.

The following examples are provided for the purposes of illustration, and not limitation.

EXAMPLES

Example 1

The Preparation and Properties of Representative Polymeric Polycarboxylic Acid Crosslinked Fibers: Polyacrylic Acid Crosslinked Fibers In this example, the preparation and properties of fibers that are crosslinked with a representative polymeric polycarboxylic acid of the invention are described. Fiber sheets composed of individual cellulose fibers (commercially available from Weyerhaeuser Company under the designation NB416) were treated with polyacrylic acid (self-catalyzing) having a molecular weight of about 3,500 grams/mole (commercially available under the designation Acumer 9930 from Rohm & Haas) according to the following procedure.

Briefly, the fiber sheet was fed from a roll through a constantly replenished bath of an aqueous polyacrylic acid solution adjusted to concentrations to achieve the desired level of polyacrylic acid addition to the fiber sheet. The treated fiber sheet was then moved through a roller nip set to remove sufficient solution to provide a fiber sheet having a moisture content of about 50%. After passing through the roll nip, the wet fiber sheet was fiberized by feeding the sheet through a hammermill. The resulting fibers were blown through a flash dryer to a cyclone where the treated cellulose fibers were collected. The curing of the treated fibers was completed by placing the fluff fibers in a laboratory oven and heating at 380° F. for five minutes. The absorbent capacity and bulk of fibers prepared as described above were determined by the following procedures.

The Fiber Absorption Quality Analyzer (Weyerhaeuser Co., Federal Way, WA) is used to determine bulk properties (wet and dry), absorbent capacities, and wet resilience of pulp fibers.

In the procedure, a 4-gram sample of the pulp fibers is put through a pinmill to open the pulp and then air-laid into a tube. The tube is then placed in the FAQ Analyzer. A plunger then descends on the fluff pad at a pressure of 0.6 kPa and the pad height bulk determined. The weight is increased to achieve a pressure of 2.5 kPa and the bulk recalculated. The result, two bulk measurements on the dry fluff pulp at two different pressures. While under the 2.5 kPa pressure, water is introduced into the bottom of the tube (bottom of the pad). The time required for the water to reach the plunger is measured. From this the absorption time and absorption rate are determined. The final bulk of the wet pad at 2.5 kPa is also measured. The plunger is then withdrawn from the tube and the wet pad allowed to expand for 60 seconds. The plunger is reapplied at 0.6 kPa and the bulk determined. The final bulk of the wet pad at 0.6 kPa is considered the wet bulk (cc/g) of the pulp product. The capacity is determined by weighing the wet pad after the water is drained from the equipment, and reported as grams water per gram dry pulp.

The absorbent capacity and wet bulk of crosslinked fibers having from 1 to 4% by weight polyacrylic acid on the fiber, prepared as described above, are summarized in Table 1. In addition, sheets containing a combination of polyacrylic acid crosslinked fibers prepared as described above and untreated fibers, in the ratio of 2:1, were prepared and their sheet bulk measured. These dry bulk measurements are also summarized in Table 1.

TABLE 1

Polyacrylic acid crosslinked fiber capacity and bulk

| Percent Polyacrylic Acid on Fiber | Absorbent Capacity (g/g) | Wet Bulk at 0.6 kPa (cc/g) | Bulk of Sheets at 66% Treated Fiber (cc/g) |
| --- | --- | --- | --- |
| 1% | 14.7 | 12.7 | 10.8 |
| 2% | 15.2 | 13.9 | 13.5 |
| 3% | 16.1 | 15.1 | 15.2 |
| 4% | 17.4 | 16.8 | 16.0 |

The results summarized in Table 1 illustrate that increasing the amount of polycarboxylic acid on the fiber increases the absorbent capacity of the fiber, and also increases the bulk of sheets prepared from polycarboxylic acid crosslinked fibers.

The resilience of polyacrylic acid crosslinked fibers prepared as described above was compared to other fibers similarly prepared with other crosslinking agents. The results presented as percent springback are summarized in Table 2. Fiber springback is determined by measuring the increase in fiber bulk on relaxing the pressure exerted on the fibers. The percent springback reported below represents the percent increase in fiber bulk upon a decrease in applied pressure from 2.5 kPa to 0.6 kPa.

TABLE 2

Springback of various crosslinked fibers.

| Crosslinking Agent (Fluff Pulp) | Percent Springback |
| --- | --- |
| DMDHEU (NB416) | 16.5 |
| DMDHU(NB416) | 20.6 |
| Citric Acid (NF405) | 14.7 |
| 4% Polyacrylic acid (NB416) | 26.4 |
| 6% Polyacrylic acid (NB416) | 29.4 |

As shown in Table 2 above, the resilience of the polycarboxylic acid crosslinked fibers is significantly greater than that observed for either urea-based (i.e., DMDHEU) or citric acid crosslinked fibers. In addition, the amount of springback observed for polyacrylic acid crosslinked fibers increases with increasing polyacrylic acid on the fiber.

The absorbent capacity (grams water/gram fiber) of polyacrylic acid crosslinked cellulose fibers prepared as described above and cured at temperatures from 330° F. to 380° F. was determined. The results for these crosslinked fibers as a function of cure temperature are summarized in Table 3.

TABLE 3

Absorbent capacity of polyacrylic acid (PAA) crosslinked fibers at various cure temperatures.

| | Absorbent Capacity (g/g) | | |
| --- | --- | --- | --- |
| Temperature ° F. | 2% PAA | 4% PAA | 6% PAA |
| 330 | 12.7 | 13.2 | 13.3 |
| 340 | 13.4 | 13.6 | 13.8 |
| 360 | 13.8 | 14.8 | 15.0 |
| 380 | 14.7 | 15.2 | 16.1 |

Table 3 illustrates that for a particular crosslinking treatment the absorbent capacity increases with increasing cure temperature. The results indicate that increasing the cure temperature increases the amount of crosslinking (i.e., ester bond formation between the polycarboxylic acid and the fiber) and that increased fiber crosslinking provides increased fiber absorbent capacity. The results summarized in Table 3 also indicate that, to an extent, increasing the amount polycarboxylic acid crosslinking agent on the fiber increases the absorbent capacity of the crosslinked fiber. Referring to the table, increasing the amount of polycarboxylic acid on the fiber from 2 to 4% generally provides a greater increase in the absorbent capacity than when the amount of polycarboxylic acid on the fiber is increased from 4 to 6% by weight of the total fibers.

Example 2

The Preparation and Properties of Fibers Crosslinked with a Representative Polymeric Polycarboxylic Acid in the Presence of Crosslinking Catalyst In this example, the preparation and properties of fibers crosslinked with a representative polymeric polycarboxylic acid, polyacrylic acid, and cured in the presence of a representative crosslinking catalyst, sodium hypophosphite, are described. The crosslinked fibers were prepared as generally described in Example 1 above.

The fibers were treated with polyacrylic acid to provide fibers having 2% polyacrylic acid on the fiber and using sodium hypophosphite as a catalyst present at a ratio of 1:10 by weight relative to the polyacrylic acid. The treated fibers were cured at temperatures from 330° F. to 380° F. and the absorbent capacity and wet bulk were measured by the procedures described in Example 1 above. The results are summarized in Table 4.

TABLE 4

Absorbent capacity and wet bulk of polyacrylic acid crosslinked fibers at various cure temperatures.

| Cure Temperature ° F. | Absorbent Capacity (g/g) | Wet Bulk at 0.6 kPa (cc/g) |
| --- | --- | --- |
| 320 | 11.1 | 10.8 |
| 330 | 13.6 | 13.2 |
| 340 | 14.2 | 13.8 |
| 360 | 15.2 | 14.9 |
| 380 | 15.9 | 15.6 |

As noted in Example 1 above, for the polycarboxylic acid crosslinked fibers of the invention, absorbent capacity and bulk increase with increasing cure temperature. Table 4 illustrates that at a given cure temperature, fibers crosslinked with polyacrylic acid in the presence of a crosslinking catalyst have absorbent capacity and bulk greater than fibers similarly crosslinked in the absence of a crosslinking catalyst. The results indicate that, for a given cure temperature and level of polycarboxylic acid on the fiber, greater crosslinking occurs (i.e., more ester bonds are formed between the crosslinking agent and the fiber) in the presence of a crosslinking catalyst. For example, referring to Tables 3 and 4, at 2% crosslinking agent on the fiber, the absorbent capacity of crosslinked fibers prepared without a catalyst at a cure temperature of 360° F. (13.8 g/g, see Table 3) was only slightly greater than that of fibers prepared with a catalyst at 330° F. (13.6 g/g, see Table 4).

Example 3

The Preparation and Properties of Fibers Crosslinked with a Representative Polymeric Polycarboxylic Acid Crosslinking Agent Blend: Polyacrylic Acid and Maleic Acid In this example, the preparation and properties of fibers crosslinked with a representative blend of crosslinking agents including a polymeric polycarboxylic acid, polyacrylic acid, and a second crosslinking agent, maleic acid, are described. The crosslinked fibers were prepared as generally described in Example 1 above.

The effect of cure temperature on the absorbent capacity and bulk of fibers crosslinked with the crosslinking blend was compared to fibers treated with polyacrylic acid alone.

The results are summarized in Table 5 below. In the table, Blend One refers to fibers crosslinked with polyacrylic acid having a molecular weight of about 2,000 grams/mole and maleic acid, and Blend Two refers to fibers crosslinked with polyacrylic acid having a molecular weight of about 3,000 grams/mole and maleic acid.

TABLE 5

Absorbent capacity (g/g) and wet bulk (cc/g) of fibers treated with polyacrylic acid and maleic acid compared with polyacrylic acid crosslinked fibers at various cure temperatures.

| Cure Temperature | Blend One | | Blend Two | | Polyacrylic Acid | |
|---|---|---|---|---|---|---|
| ° F. | Capacity | Bulk | Capacity | Bulk | Capacity | Bulk |
| 330 | 14.9 | 14.8 | 15.0 | 14.7 | 13.6 | 13.2 |
| 340 | 15.3 | 15.1 | 15.4 | 15.1 | 14.2 | 13.8 |
| 360 | 15.9 | 15.7 | 16.2 | 16.0 | 15.2 | 14.9 |
| 380 | 16.5 | 16.2 | 16.8 | 16.6 | 15.9 | 15.6 |

Table 5 illustrates that, at all cure temperatures examined, absorbent capacity and bulk of fibers crosslinked with a polycarboxylic acid combination of polyacrylic acid and maleic acid are greater than for fibers crosslinked with polyacrylic acid alone. Referring to the data for the two blends, the greater absorbent capacity and bulk observed for Blend Two containing polyacrylic acid of molecular weight about 3,000 grams/mole, may indicate that the higher molecular weight polyacrylic acid provides increased crosslinking, and hence increased absorbent capacity and bulk, relative to Blend One containing a polyacrylic acid having a somewhat lower molecular weight (i.e., 2,000 grams/mole).

Example 4

Methods for Forming Representative Polymeric Polycarboxylic Acid Crosslinked Cellulosic Fibers: Polymaleic Acid Crosslinked Fibers This example illustrates methods for forming representative polymaleic acid polymer crosslinked cellulosic fibers of the present invention.

Pulp sheets were treated with polymaleic acid (Acumer 4210, Rohm & Haas) according to the following procedure. The pulp sheet (prepared from southern bleached kraft pulp commercially available from Weyerhaeuser Company under the designation NB416) was fed from a roll through a constantly replenished bath of the chemical crosslinking solution. The treated sheet was then passed through a roller nip set to remove sufficient solution so that the treated pulp sheet had a 50% moisture content. The concentration of the crosslinking agent in the bath was adjusted to achieve the desired level of chemical addition to the pulp sheet. Sodium hypophosphite was used as the catalyst at a level of 1:10 (catalyst:crosslinking agent). After passing the treated sheet through the roll nip, the sheet was fed through a hammermill to fiberize the pulp. The fiberized pulp was then blown through a flash dryer to a cyclone where the treated fluff was collected. The curing of the treated pulp was completed by placing the fluff pulp in an oven at the cure temperature (e.g., 320° to 380° F.) for five minutes.

The performance characteristics (bulk, capacity, acquisition rate, knot level) of representative polymaleic acid polymer crosslinked fibers formed by the above method are described in Examples 5 through 8.

Example 5

Bulk and Absorbent Capacity of Representative Polymaleic Acid Crosslinked Cellulosic Fibers This example illustrates the bulk and absorbent capacity of fibrous mats formed from representative polymaleic acid crosslinked cellulosic fibers of the present invention.

Representative polymaleic acid crosslinked fibers were prepared as described in Example 4 above. Briefly, southern pine pulp fibers (Weyerhaeuser Co. designation NB416) were treated with varying amounts of a polymaleic acid crosslinking agent (Acumer 4210, Rohm & Haas) and cured at several temperatures. The bulk and absorbent capacity of the fiber were determined by the procedures described in Example 1 above.

The bulk and absorbent capacity of mats formed from representative polymaleic acid crosslinked fibers prepared from NB416 pulp fibers and varying amounts of Acumer 4210 (i.e., 2, 3, 4, 6, and 8 percent by weight of fibers) at cure temperatures of 340° F. and 360° F. are summarized in Tables 6 and 7, respectively.

TABLE 6

Polymaleic Acid Crosslinked Fiber Bulk and Capacity: Cure Temperature 340° F.

| Percent Polymaleic Acid on Pulp | Bulk, cc/g | Capacity, g/g |
|---|---|---|
| 2 | 15.6 | 15.6 |
| 3 | 16.2 | 16.3 |
| 4 | 16.9 | 17.1 |
| 6 | 17.8 | 18.1 |
| 8 | 19.1 | 18.5 |

TABLE 7

Polymaleic Acid Crosslinked Fiber Bulk and Capacity: Cure Temperature 360° F.

| Percent Polymaleic Acid on Pulp | Bulk, cc/g | Capacity, g/g |
|---|---|---|
| 2 | 16.2 | 16.3 |
| 3 | 16.6 | 16.9 |
| 4 | 17.3 | 17.3 |
| 6 | 18.8 | 18.7 |
| 8 | 19.8 | 18.5 |

Generally, increasing polymaleic acid polymer crosslinking agent on the fiber results in fibers having increased bulk and capacity.

The effect of cure temperature variation (i.e., from 320° F. to 380° F.) on the bulk and absorbent capacity of two representative polymaleic acid crosslinked fibers (i.e., 2 and 4 percent by weight Acumer 4210 on NB416 pulp fibers) prepared as described above in Example 4 is summarized in Table 8.

TABLE 8

Polymaleic Acid Crosslinked Fiber Bulk and Capacity: Effect of Cure Temperature.

| Temperature, ° F. | 2% Polymaleic Acid on Pulp | | 4% Polymaleic Acid on Pulp | |
|---|---|---|---|---|
| | Bulk, cc/g | Capacity, g/g | Bulk, cc/g | Capacity, g/g |
| 320 | 14.4 | 14.6 | 15.7 | 15.5 |
| 340 | 15.6 | 15.6 | 16.6 | 16.3 |
| 360 | 16.2 | 16.3 | 17.4 | 17.3 |
| 380 | 16.8 | 16.7 | 17.8 | 17.9 |

Generally, increasing cure temperature results in increased bulk and capacity.

Example 6

Liquid Acquisition Rate of Representative Polymaleic Acid Crosslinked Cellulosic Fibers In this example, the liquid acquisition rates for absorbent articles incorporating representative polymeric polycarboxylic acid crosslinked fibers of the present invention are compared to the acquisition rate for an absorbent article incorporating a control DMDHEU crosslinked fiber. Polymaleic acid crosslinked fibers were prepared by the method described in Example 4 above. Briefly, southern pine pulp fibers (Weyerhaeuser Co. designation NB416) were crosslinked with a polymaleic acid polymer crosslinking agent (Acumer 4210, Rohm & Haas) at 3 and 4 percent by weight crosslinking agent based on total weight of the fibers and cured at 360° F.

The treated fibers were then formed into acquisition patches by airlaying the fibers into a 300 g/m² pad. The pad was pressed at 500 psi and cut into patches that were placed into a commercially available diaper (Kimberly-Clark) in place of the diaper's acquisition layer. The liquid acquisition rates for absorbent articles incorporating the fibrous patches were then determined by the procedure described below.

Procedure for Determining Liquid Acquisition Rate

The acquisition rates for absorbent articles containing representative polymaleic acid crosslinked fibers were determined by incorporating the fibers into a commercially available diaper (Kimberly-Clark) and comparing the acquisition time to a control diaper modified to include a DMDHEU crosslinked fiber (NHB416 commercially available from Weyerhaeuser Co., Federal Way, Wash.). The acquisition time was determined in accordance with the procedure described below.

Briefly, the procedure measures the time required for each of three liquid doses of synthetic urine to wick into the product.

The test samples were prepared by modifying commercially available diapers. the top nonwoven layer of a commercial diaper was carefully peeled back and the diaper's acquisition layer removed. The absorbent structures (i.e., patches of polymaleic acid polymer crosslinked fibers and control DMDHEU crosslinked fibers) were then inserted into the diaper and the nonwoven layer repositioned.

Once the sample is prepared, the sample is marked with an "X" one inch from the center of the fluff mat toward the front of the diaper. A dosing ring (stainless steel, 3 inches high with a 2-inch ID is placed over the X. A funnel containing 100 ml of synthetic urine is positioned over the ring. The fluid is applied within the dosing ring by opening the stopcock at the base of the funnel. The time in seconds is measured from the time the funnel is opened until the liquid wicks into the product from the bottom of the dosing ring. This is repeated two additional times with a 20-minute wait between doses. The acquisition rate is calculated by dividing the 100 ml by the time taken to absorb the liquid for each dose.

Liquid acquisition time is reported as either the length of time (seconds) necessary for the liquid to be absorbed into the product for each of the three doses, or the rate (ml/sec) that a liquid is absorbed into the product for each of the doses.

The aqueous solution used in the tests is a synthetic urine available from National Scientific under the trade name RICCA. The synthetic urine is a saline solution containing 135 meq./l sodium, 8.6 meq./l calcium, 7.7 meq./l magnesium, 1.94% urea by weight (based on total weight), plus other ingredients.

The liquid acquisition rates for the absorbent articles containing the representative polymaleic acid crosslinked fibers (i.e., crosslinked NB416 pulp fibers treated with 3 and 4 percent by weight polymaleic acid) and the control DMD-HEU crosslinked fiber (i.e., NHB416 pulp fibers) are summarized in Table 9 below.

TABLE 9

Liquid Acquisition Rate for Absorbent Articles Containing Polymaleic Acid Crosslinked Fiber.

| Crosslinking Agent | Liquid Acquisition Rate (mL/sec) | | |
|---|---|---|---|
| | Dose 1 | Dose 2 | Dose 3 |
| DMDHEU | 5.5 | 3.03 | 2.04 |
| 3% Polymaleic acid | 8.33 | 5.00 | 3.12 |
| 4% Polymaleic acid | 8.33 | 5.26 | 3.57 |

As sown in FIG. 1 and Table 9, the liquid acquisition rates for the absorbent articles containing polymaleic acid crosslinked fibers was significantly greater than for the corresponding article containing fibers crosslinked with DMDHEU.

Example 7

Knot Level of Representative Polymaleic Acid Crosslinked Fluff Pulp

This example illustrates the low knot level of polymaleic acid crosslinked fluff pulp formed in accordance with the present invention. The level of knots in representative polymaleic acid crosslinked fluff pulp was determined by a sonic fractionation process. Briefly, the sonic fractionation system uses a combination of low frequency sound vibrations and an airstream to separate fibers by their size.

In the process, 5 grams of crosslinked fluff pulp were evenly distributed over a 5 mesh screen. The screen was then placed on top of a screen stack consisting of 8, 12, 60, and 200 mesh screens. A speaker was placed on top of the screen stack and attached to a tuner to produce a 13 Hz tone. An airstream was also directed through the screen stack to assist in the distribution of agitated fibers through the screens. After six minutes, the tone and airstream were discontinued and the fluff pulp distributed on each screen was weighed. The fluff pulp knot level (reported as percent knots) was determined by taking the total weight of the fluff pulp on the 5, 8, and 12 mesh screens and dividing by the starting weight of the fluff pulp.

Crosslinked fluff pulp was prepared by a wet laid method as described above in Example 4. For this example, the pulp fibers contained 6% by weight polymaleic acid. The knot level for this polymaleic acid crosslinked fiber and a control fluff pulp crosslinked with dimethyloldihydroxy ethylene urea (DMDHEU) was determined by the sonic fractionation method described above. The results are summarized in Table 10 below.

TABLE 10

Polymaleic Acid Crosslinked Fluff Pulp Knot Level.

| Crosslinking Agent | Fluff Pulp Percent Knots |
|---|---|
| Polymaleic Acid | 4.2% |
| DMDHEU | 21% |

The level of knots for the polymaleic acid crosslinked fluff pulp is significantly less than for fluff pulp similarly crosslinked with DMDHEU.

Example 8

The Effect of pH on Absorbent Capacity of Representative Polymaleic Acid Crosslinked Fibers In this example, the effect of pH of the crosslinking reaction on absorbent capacity of fibrous mats crosslinked with polymaleic acid was determined. Pulp was treated with 4% polymaleic acid as described above in Example 4. The chemical treatment bath was adjusted to different pH levels using either concentrated aqueous hydrochloric acid or sodium hydroxide, as needed. The capacity of fibrous mats prepared from fluff pulp crosslinked with polymaleic acid at various pH (i.e., 2.0, 2.5, 3.0, 3.5, and 4.0) and cured at various temperatures (i.e., 320, 340, 360, and 380° F.) was determined as described in Example 1. The results are summarized in Table 11.

TABLE 11

Polymaleic Acid Crosslinked Fiber Absorbent Capacity: Effect of Crosslinking Solution pH.

| Cure Temperature ° F. | Absorbent Capacity (g/g) | | | | |
|---|---|---|---|---|---|
| | pH 2.0 | pH 2.5 | pH 3.0 | pH 3.5 | pH 4.0 |
| 320 | 16.5 | 16.6 | 16.3 | 15.9 | 15.2 |
| 340 | 17.4 | 17.2 | 16.9 | 16.8 | 15.9 |
| 360 | 18.0 | 18.2 | 17.9 | 17.0 | 17.2 |
| 380 | 19.0 | 18.9 | 18.5 | 17.6 | 17.9 |

The results demonstrate that polymaleic acid crosslinking at pH from about 2 to about 3 provides crosslinked fibers having the greatest absorbent capacity.

Example 9

Fiber Acquisition Quality of Representative Polymaleic Acid Crosslinked Cellulosic Fibers This example compares the fiber acquisition quality (FAQ) including bulk and absorbent properties (i.e., wet and dry bulk, absorption time, and absorbent capacity) of fibers crosslinked with representative polymaleic acid polymer (i.e., Belclene 200) and polymaleic acid copolymer (i.e., Belclene 283 prepared by the hydrolysis of the polymer formed by the polymerization of maleic anhydride, ethyl acrylate, and vinyl acetate), commercially available from FMC Corp. The properties of the crosslinked fibers were also compared to those of a noncrosslinked pulp fiber (NB416).

Briefly, crosslinked fibers were prepared by treating pulp fibers with an aqueous solution containing 6 percent by weight crosslinking agent and 1.5 percent by weight sodium hypophosphite, based on total weight of fibers, at pH about 2.0. The crosslinking agent solution was applied to a pulp sheet of NB416 southern pine fluff grade pulp to give a pulp consistency of approximately 50% solids. The sheet was then fed twice through a pinmill in an airlay pad former to fiberize the pulp. The 20-gram fluff pad was then cured in a through-air thermobonder at 192° C. for two minutes. All samples were conditioned and tested in a 50% relative humidity environment.

The wet and dry bulk and absorptive capacity of the sheets formed from various polycarboxylic acid crosslinked fibers were determined by the procedures described in Example 1 above. The absorption time was determined by the procedure described in Example 6 above. The results for the various polycarboxylic acid crosslinked fibers and the control fiber are summarized in Table 12.

TABLE 12

The Effect of Crosslinking Agent on Fiber Acquisition Quality.

| Crosslinking Agent | Absorption Time seconds | Wet Bulk at 0.6 kPa cc/g | Absorbent Capacity g/g |
|---|---|---|---|
| NB416 Control | 3.6 | 12.1 | 12.6 |
| Belclene 200 | 3.2 | 17.9 | 17.9 |
| Belclene 283 | 3.8 | 170 | 17.4 |

Fibers crosslinked with representative maleic acid copolymers had absorption times comparable to non-crosslinked cellulose fibers and enhanced wet bulk and absorbent capacity relative to the noncrosslinked fibers.

Example 10

Bulk and Absorbent Capacity of Representative Cellulosic Fibers Crosslinked With a Blend of Polyacrylic Acid and Citric Acid This example illustrates the bulk and absorbent capacity of fibrous mats formed from representative cellulose crosslinked with a blend of polyacrylic acid and citric acid.

Representative cellulose fibers crosslinked with a blend of polyacrylic acid and citric acid were prepared as generally described in Example 1 above. Briefly, southern pine pulp fibers (Weyerhaeuser Company designation NB416) were treated with a crosslinking agent blend of polyacrylic acid and citric acid of varying compositions and then cured. The bulk and absorbent capacity of the resulting fibers were determined by the procedures described above in Example 1.

The bulk and absorbent capacity for fibers crosslinked with (1) polyacrylic acid (i.e., 4%, 6%, 8% by weight polyacrylic acid based on the total weight of fibers); (2) polyacrylic acid/citric acid blends; and (3) blends of low molecular weight polycarboxylic acids (i.e., maleic acid blends with citric acid and itaconic acid) are summarized in Table 13.

TABLE 13

Crosslinked Fiber Bulk and Capacity.

| Crosslinked Fiber | Wet Bulk at 0.6 kpa cc/g | Absorbent Capacity g/g |
|---|---|---|
| 4% PAA | 17.3 | 17.3 |
| 6% CA | 17.0 | 17.2 |
| 6% PAA | 18.8 | 18.7 |
| 2% PAA/4% CA | 20.9 | 21.1 |
| 3% PAA/3% CA | 21.4 | 21.3 |
| 2% PAA*/4% CA | 20.9 | 21.0 |
| 3% PAA*/3% CA | 20.6 | 20.4 |
| 2% MA/4% CA | 20.1 | 20.1 |
| 3% MA/3% CA | 19.3 | 19.2 |
| 3% MA/3% IA | 18.1 | 18.5 |
| 8% PAA | 19.8 | 18.5 |
| 2% PAA/6% CA | 22.2 | 22.2 |
| 2% PAA*/6% CA | 21.2 | 21.1 |

In Table 13, PAA refers to polyacrylic acid having a molecular weight of about 3500; PAA* refers to polyacrylic acid having a molecular weight of about 10,000; CA refers to citric acid; MA refers to maleic acid; and IA refers to itaconic acid.

Referring to Table 13, the bulk and capacity generally increase with increasing amounts of polyacrylic acid crosslinking agent. For those crosslinked fibers having 6% crosslinking agent by weight of total fibers, fibers crosslinked with the polyacrylic acid/citric acid blends have greater bulk and capacity than those fibers with the same crosslinking agent add-on level and crosslinked either with polyacrylic acid alone or blends of lower molecular weight polycarboxylic acids. The same trend is observed for crosslinked fibers treated with 8% crosslinking agent by weight of the total fibers. These results demonstrate that polyacrylic acid/citric acid crosslinking agent blends provide crosslinked fibers having improved bulk and capacity relative to fibers crosslinked with polyacrylic acid alone or low molecular weight polycarboxylic acid blends. Also, fibers crosslinked with 6% citric acid have a lower bulk and absorbent capacity compared to fibers crosslinked with the same amount of polyacrylic acid.

Example 11

Resistance to Density Reversion For Representative Polymeric Polycarboxylic Acid Crosslinked Fibers In this example, the resistance to aging or reversion of the density of webs formed from the polymeric polycarboxylic acid crosslinked fibers of the present invention is described. Generally, the polymeric polycarboxylic acid crosslinked fibers of this invention exhibit a density that remains substantially unchanged over the lifetime of fibrous webs prepared from such fibers. In contrast, citric acid crosslinked fiber pulps show a considerable increase in density resulting from a loss of bulk that is accompanied by a loss of absorbent capacity over time. Generally, an increase in density indicates a decrease in the level of crosslinking (i.e., reversion) in the fibrous web. The loss of crosslinking in the fibrous web results in a less bulky web and, consequently, diminished absorbent capacity and liquid acquisition capability. The effect of aging (i.e., reversion of crosslinking) on the density of a fibrous web composed of a representative polyacrylic acid crosslinked fibers of the present invention and a fibrous web composed of citric acid crosslinked fibers (each 6% by weight crosslinking agent based on total weight of fibers) is described below.

The aging of crosslinked pulp was simulated by a general method for accelerated aging in which the pulp sample was placed in a controlled humidity oven 85 to 87% humidity at 80° C. for 16 hours. In the method, the samples were then removed from the oven and allowed to equilibrate in a 50% humidity environment at room temperature for 8 hours prior to determining the density of the fibrous webs. The effect of accelerated aging on the density of fibrous pads having a basis weight of 400 g/m² which were densified at 5,000 psi is shown in Table 14.

TABLE 14

Density of Fibrous Webs of Crosslinked Fibers.

| | Density (g/cm³) | | |
|---|---|---|---|
| Crosslinked Fiber | As Produced | Simulated Aging | Percent Increase |
| 6% PAA | 0.169 | 0.174 | 3.0 |
|  | .186 | 0.183 | −1.6 |
| 6% CA | 0.147 | 0.217 | 47.6 |
|  | 0.147 | 0.211 | 43.5 |
| 4% PAA/4% CA | 0.104 | 0.110 | 5.7 |

The results indicate that the density of fibrous webs composed of polyacrylic acid crosslinked fibers remains substantially unchanged after accelerated aging. In contrast, the density of fibrous webs composed of citric acid crosslinked fibers increased significantly, by about 50%. The results show that fibers crosslinked with a blend of polyacrylic acid and citric acid also resist density increase.

The effect of accelerated aging on the bulk and capacity of fibrous webs composed of polymaleic acid crosslinked fibers was also determined. The fluff pulp was prepared as described above in Example 4 and subjected to the accelerated aging process described above. The bulk and absorbent capacity of these fibrous webs were measured before and after the accelerated aging process. The results are summarized in Table 15.

TABLE 15

Bulk and Absorbent Capacity of Polymaleic Acid Crosslinked Fibers: Accelerated Aging.

| Polymaleic Acid Crosslinked Fiber | Wet Bulk, at 0.6 kPa cc/g | Absorbent Capacity g/g |
|---|---|---|
| As Produced | 15.3 | 15.4 |
| Simulated Aging | 15.4 | 15.7 |
| Percent Change | +0.7 | +2.0 |

The results indicated that the accelerated aging process has no effect on the polymaleic acid crosslinked fluff pulp as indicated by insignificant changes in the bulk and absorbent capacity of these webs.

These results indicate that polymeric polycarboxylic acid crosslinked fibers (e.g., fibers crosslinked with polyacrylic acid or polymaleic acid) retain their crosslinks over time and thereby provide fibrous webs that do not substantially increase in density nor decrease in bulk or absorbent capacity over time.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An absorbent composite comprising cellulosic fibers intrafiber crosslinked with a polymaleic acid crosslinking agent, wherein the polymaleic acid crosslinking agent is a polymer selected from the group consisting of a polymaleic acid polymer, a copolymer of maleic acid and a monoalkyl substituted phosphinate, a copolymer of maleic acid and a monoalkyl substituted phosphonate, a copolymer of maleic acid and a comonomer, and mixtures thereof, wherein the comonomer is selected from the group consisting of vinyl acetate, methyl vinyl ether, and itaconic acid.

2. The composite of claim 1 wherein the polymaleic acid crosslinking agent comprises a polymaleic acid polymer.

3. The composite of claim 1 wherein the polymaleic acid crosslinking agent comprises a copolymer of maleic acid and a monoalkyl substituted phosphinate.

4. The composite of claim 1 wherein the polymaleic acid crosslinking agent comprises a copolymer of maleic acid and a monoalkyl substituted phosphonate.

5. The composite of claim 1 wherein the polymaleic acid crosslinking agent comprises a copolymer of maleic acid and a comonomer, and wherein the comonomer is selected from the group consisting of vinyl acetate, methyl vinyl ether, and itaconic acid.

6. The composite of claim 1 wherein the fibers have between about 0.2 weight percent and about 20 weight percent polymaleic acid crosslinking agent, calculated on a dry fiber weight basis, reacted therewith.

7. The composite of claim 1 wherein the polymaleic acid crosslinking agent comprises a low pH polymaleic acid having a pH of from about 2 to about 4.

8. The composite of claim 1 wherein intrafiber crosslinked cellulosic fibers are further crosslinked with a second crosslinking agent.

9. The composite of claim 8 wherein the second crosslinking agent is selected from the group consisting of citric acid, maleic acid, itaconic acid, glyoxal, glycolic acid, and urea-based crosslinking agents.

10. The composite of claim 8 wherein the second crosslinking agent is citric acid.

11. The composite of claim 1 further comprising non-crosslinked cellulosic fibers.

12. The composite of claim 1 further comprising cellulosic fibers crosslinked with at least one crosslinking agent chosen from a urea-based crosslinking agent, a C2–C8 dialdehyde crosslinking agent, or a C2–C9 polycarboxylic acid crosslinking agent.

13. An absorbent article comprising the composite of claim 1.

14. The article of claim 13 wherein the article is a diaper.

15. The article of claim 13 wherein the article is a feminine care product.

16. An absorbent composite comprising cellulosic fibers intrafiber crosslinked with a polymaleic acid polymer.

17. The composite of claim 16 further comprising non-crosslinked cellulosic fibers.

18. An absorbent article comprising the composite of claim 16.

19. The article of claim 18 wherein the article is a diaper.

20. The article of claim 18 wherein the article is a feminine care product.

* * * * *